United States Patent
Tinti et al.

(12) 
(10) Patent No.: US 6,566,552 B2
(45) Date of Patent: May 20, 2003

(54) INDUSTRIAL PROCESS FOR THE PRODUCTION OF L-CARNITINE

(75) Inventors: Maria Ornella Tinti, Rome (IT); Oreste Piccolo, Sirtori (IT); Fausto Bonifacio, Latina (IT); Cristina Crescenzi, Rome (IT); Sergio Penco, Milan (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 09/849,363

(22) Filed: May 7, 2001

(65) Prior Publication Data

US 2002/0165408 A1 Nov. 7, 2002

Related U.S. Application Data

(63) Continuation of application No. PCT/IT99/00365, filed on Nov. 12, 1999.

(30) Foreign Application Priority Data

Nov. 16, 1998 (IT) .......................... MI98A2477

(51) Int. Cl.$^7$ ............................................ C07C 229/00
(52) U.S. Cl. ....................... 562/567; 560/170
(58) Field of Search .................... 562/567; 560/170

(56) References Cited

U.S. PATENT DOCUMENTS 5,510,503 A * 4/1996 Laue et al.
5,599,954 A * 2/1997 Mitsuhashi et al.
5,614,031 A   3/1997 Genet et al.

FOREIGN PATENT DOCUMENTS

| EP | 0 295 109 | 12/1988 |
| EP | 0 339 764 | 11/1989 |
| EP | 0 375 417 | 6/1990 |
| WO | WO96/01831 | 1/1996 |
| WO | WO99/52915 | 10/1999 |

* cited by examiner

Primary Examiner—Johann Richter
Assistant Examiner—Paul A. Zucker
(74) Attorney, Agent, or Firm—Nixon & Vanderhye P.C.

(57) ABSTRACT

The present invention describes a process for the industrial production of L-carnitine, comprising the enantioselective reduction of an alkyl 4-chloro-3-oxobutyrate or 4-chloro-3-oxobutyramide. The optically active 3-hydroxy derivative thus obtained is reacted with trimethylamine, obtaining crude L-carnitine, which is then finally purified. The catalyst used for the reduction is a complex of ruthenium bound to a penta-atomic bis-heteroaromatic system. The reduction reaction, performed in controlled conditions of hydrogen pressure, substrate concentration, temperature, and substrate: catalyst molar ratio, enables 4-chloro-3-hydoxybutyrate or 4-chloro-hydroxybutyamide to be obtained in a high yield. The process described, which leads to L-carnitine being obtained, is easily applicable on an industrial scale.

11 Claims, No Drawings

INDUSTRIAL PROCESS FOR THE PRODUCTION OF L-CARNITINE

This application is a continuation of PCT/IT99/00365 filed Nov. 12, 1999

FIELD OF THE INVENTION

The invention described herein relates to the synthesis of L-carnitine.

The subject of the invention is a process for obtaining this product, which can be easily implemented on an industrial scale.

STATE OF THE ART

Carnitine contains an asymmetry centre and can therefore exist in the form of two enantiomers, designated R-(−)-carnitine and S-(+)-carnitine, respectively. Of these, only R-(−)-carnitine is present in living organisms where it acts as a carrier for the transport of fatty acids across the mitochondrial membranes.

It is therefore essential that only R-(−)-carnitine be administered to patients undergoing regular haemodialysis treatment or treated for cardiac or lipid metabolism disorders.

In view of the substantial biological and pharmaceutical interest in this molecule, many studies have been conducted with a view to its synthesis.

The known techniques of large-scale synthesis of L-carnitine include:
  i) the optical resolution of a racemic mixture: this technique involves the use of a resolving agent in an equimolar amount and the separation of the unwanted enantiomer. This procedure leads to the loss of 50% of the starting product.
  ii) Stereospecific hydration of crotonobetaine or γ-butyrobetaine by a microbiological method (U.S. Pat. No. 4,708,936). This microbiological synthesis procedure entails the risk of imperfect reproducibility, of possible alterations of the strain used, and of possible biological contamination of the product.
  iii) Enantioselective reduction of a butyric 4-chloro-3-oxoester by means of mono- or bimetallic ruthenium catalysts. This yields the corresponding 3-hydroxy derivative which, by reaction with trimethylamine and hydrolysis of the ester group, is converted to L-carnitine.

The reduction reaction mentioned in iii) has been the subject of several studies.

For example, patent EP-B-295109 describes the reduction of a 4-chloro-3-oxobutyrate with a catalyst containing ruthenium bound to a chiral diphosphine which in turn is bound to a bisnaphthalenic system; the valence of the metal is completed by a combination of halogens and triethylamine. The reaction is carried out at 30° C. with a hydrogen pressure ranging from 40 to 100 kg/cm$^2$, with substrate:catalyst molar ratio of 1000:1, in a reaction time of 16–20 hours. The optical yield below 67% and the lengthy reaction times and high pressures involved make the process industrially unacceptable.

In patent application EP-A-339764, L-carnitine is obtained by means of a process comprising the reaction of a 4-halo-3-oxobutyrate with the above-mentioned ruthenium-based catalyst: the reaction is carried out at approximately 100° C., at a mean pressure of 70–100 kg/cm$^2$, with a substrate:catalyst molar ratio ranging from 1000 to 10,000:1. The process described once again presents the disadvantage of having to operate at high pressure values. In addition, the overall carnitine yield with this method was modest (46%). Similar results are reported in Tetrahedron Letters, 29, 1555, (1988).

The synthesis methods described above not only present modest yields and, in the first case, also lengthy reaction times, but also involve operating at high hydrogen pressures, which increases the cost of the process and the safety precautions to be adopted. This problem becomes crucial when moving over from laboratory- to industrial-scale production.

A number of studies describe the reduction of β-ketoesters by means of ruthenium complexes catalysts, operating at moderate pressure values; the results. however, are unsatisfactory in terms of yields and/or reaction times, and these processes therefore cannot be applied on an industrial scale. In Tetrahedron Letters, 32, 4163, (1991), the reduction of 4-chloro-3-oxobutyrate with 4-atm. hydrogen pressure is described. The reduced product has an enantiomeric purity inferior to that obtained when operating at high pressure, and the reaction times are rather lengthy (6 h). The lower enantiomeric purity leads to a greater loss of L-carnitine yield. In EP-A-573184, the reduction of a terbutylic ester of the same substrate is carried out at a pressure of 10–15 kg/cm$^2$: the reaction is completed in two hours with an unsatisfactory yield and enantiomeric purity.

Analysis of the above-mentioned technique reveals the lack of a process for the synthesis of L-carnitine which is easily and efficiently reproducible on an industrial scale. In particular, what is lacking is an L-carnitine synthesis process comprising the enantioselective catalytic reduction of 4-halo-3-oxobutyric derivatives of such a nature as to be carried out on an industrial scale with high yields and high enantiomeric purity and operating in moderate pressure conditions.

SUMMARY OF TILE INVENTION

The present invention discloses a process for the industrial production of L-carnitine, comprising the enantioselective reduction of an alkyl 4-chloro-3-oxbutyrate or 4-chloro-3-oxobutyramide. The optically active 3-hydroxy derivative thus obtained is reacted with trimethylamine, obtaining crude L-carnitine, which is then finally purified. The catalyst used for the reduction is a complex of ruthenium bound to a penta-atomic bis-heteroaromatic system. The reduction reaction, performed in controled conditions of hydrogen pressure, substrate concentration, temperature, and substrate:catalyst molar ratio, enables 4-chloro-3-hydroxybutyrate or 4-chloro-hydroxybutyramide to be obtained in a high yeild. The process described, which leads to L-carnitine being obtained, is easily appilcable on an industrial scale.

DETAILED DESCRIPTION OF THE INVENTION

The subject of the invention described herein is a process for the synthesis of L-carnitine. The first step in achieving the object of the invention consists in the enantioselective catalytic reduction of an alkyl 4-chloro-3-oxobutyrate or 4-chloro-3-oxobutyramide, according to the following diagram:

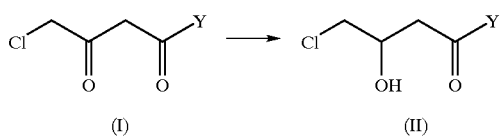

where:
Y=$OR_1$, NH—$R_1$, $N(R_1R_2)$ in which $R_1$ is H or
$R_1,R_2$, equal or different=alkyl $C_1$–$C_{10}$ alkylaryl and reaction of formula (II) derivatives with trimethylamine, with formation of L-carnitine.

The preferred starting substrate is ethyl 4-chloro-3-oxobutyrate (ethyl γ-chloro-acetoacetate).

The reduction reaction catalyst consists of a ruthenium complex bound to a penta-atomic bis-heteroaromatic system. This structure corresponds to one of the two formulas (III) or (IV).

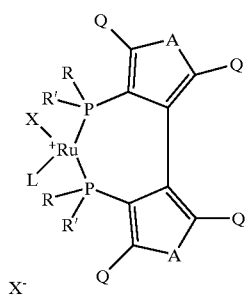

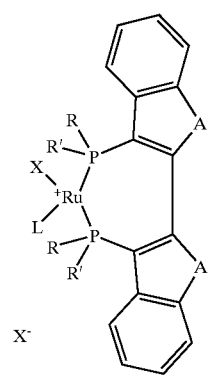

where:
A=S, O, $NR_3$, N-aryl, N—CO—$R_3$
$R_3$=alkyl $C_1$–$C_{10}$, alkylaryl, aryl
Q=alkyl $C_1$–$C_4$, phenyl
R, R', equal or different=optionally alkyl-substituted phenyl, $C_1$–$C_6$ alkyl, $C_3$–$C_8$ cycloalkyl, or R and R' together form a 4–6 atom phosphorocyclic system
X and L, equal or different, have the following meanings:
X=halogen, alkylsulphonate, arylsulphonate
L=halogen, aryl, π aryl, olefin system, $η^3$ allyl system, such as, for example, the 2-methylallyl system, carboxylate group, such as, for example, acetate or trifluoroacetate.

What is meant by the π aryl group is a type of direct co-ordination with the aromatic electron system, without any direct bonding of a carbon atom of the ring with the metal.

The formula (III) and (IV) compounds are described in patent application WO 96/01831, incorporated herein for reference.

In particular, the preference is for the use of catalysts where A represents S (3,3'-bisthiophenic structure), X represents halogen, particularly iodine, and L is an aryl system. The preferred catalyst is {[Ru (p-cymene) I (+) TMBTP] I}, represented by formula (V).

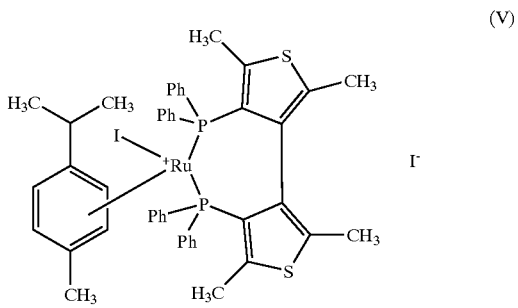

The reduction of alkyl 4-chloro-3-oxobutyrate or 4-chloro-3-oxobutyramide is done at a hydrogen pressure ranging from 2 to 7 bar, at a temperature ranging from 90 to 150° C., and with a substrate:catalyst molar ratio ranging from 5,000:1 to 30,000:1.

According to a preferred realisation of the invention, the reduction is performed at a hydrogen pressure of 5 bar, at a temperature of 120° C., and with a substrate:catalyst molar ratio between 10,000:1 and 15,000:1

The concentration of the substrate in the reaction mixture also contributes towards obtaining the reduced product in a high yield and with high-grade optical purity. This concentration ranges from 5 to 15 g of substrate per 100 ml of solvent, and the preferred concentration is 10 g/100 ml.

The reaction mixture may advantageously contain catalytic amounts of a base.

The moderate hydrogen pressure conditions (on average 5 bar) make it possible to operate with simpler reactors and with less stringent safety conditions compared to similar reactions described in the known technique requiring a pressure of 100 atmospheres.

The process described herein proves easily reproducible on an industrial scale and does not require the use of any additional expedients, such as, for example, the use of acid co-catalysts.

The process according to the invention yields optically active alkyl 4-chloro-3-hydroxybutyrate or 4-chloro-3-hydroxybutyramide with a yield≧95% and with e.e. ranging from 95 to 97%. As a result of the transformations described here below, these results make it possible to obtain the L-carnitine end product with an overall yield of 65–70%.

Furthermore, high substrate:catalyst ratios make it possible to operate with low amounts of catalyst, thus contributing to cost savings in the reaction process.

The alkyl 4-chloro-3-hydroxybutyrate or 4-chloro-3-hydroxybutyramide obtained by catalytic reaction are subsequently converted to L-carnitine reaction of formula (II) derivatives by reaction with trimethylamine.

The reduced derivatives are reacted with trimethylamine with formation of L-carnitine alkyl ester or alkyl amide. This reaction is performed preferably at temperatures from 55 to 90° C. for time periods ranging from 1 to 70 hours. Particularly satisfactory results are obtainable when operating at 65° C. for 60 hours, or at 80° C. for 24 hours. According to the type of reactor used, stirring and loading conditions, reaction times of even 1–2 hours have been observed at 80° C.

The reaction entails the substitution of the 4-chloro with the 4-trimethylamine group for and hydroylsis of the ester or amide group, with the formation of crude L-carnitine, which is then purified to make it suitable for pharmaceutical use.

The purification can be done with known methods such as, for example, chromatography, extraction with solvents, ultrafiltration, and other equivalent methods.

Thanks to the advantages identified above, such as low pressure, high yields, and high-grade optical purity, and the use of limited amounts of catalyst, the invention described herein makes it possible to produce L-carnitine efficiently and economically in large-scale industrial plant.

The invention is further described by means of the following examples.

EXPERIMENTAL PART

EXAMPLE 1

Preparation of {[Ru (p-cymene) I (+) TMBTP] I} a) Preparation of [Ru I$_2$ p-cymene]$_2$

Two g of [Ru Cl$_2$ p-cymene]$_2$ and 50 ml of methylene chloride are placed under nitrogen in a flask; 66 mg of tetramethylammonium iodide and subsequently an aqueous solution (50 ml) containing 10.2 mg of Kl are added to the solution.

The mixture is left under vigorous stirring and in an inert atmosphere for approximately 15 hours at ambient temperature. The phases are separated. The aqueous phase is extracted with 2×40 ml of CH$_2$Cl$_2$. The gathered organic phases are washed with 3×40 ml of H$_2$O, dried on Na$_2$SO$_4$ and filtered on fume silica (dicalite). A red-brown solution is obtained which is vacuum-dried. 3.07 g of [Ru I$_2$ p-cymene]$_2$ are obtained.

b) Preparation of {[Ru (p-cymene) I (+) TMBTP] I}

155 mg of [Ru I$_2$ p-cymene]$_2$ and 204 mg of (+) TMBTP are placed under nitrogen in a flask, and the mixture of 80 ml of CH$_2$Cl$_2$ and 30 ml of MeOH degassed with nitrogen is added. The mixture is left at reflux under stirring for 1.5 h; it is then cooled and concentrated at reduced pressure. The dark red solid consisting of {[Ru (p-cymene) I (+) TMBTP] I} is used as such in the enantioselective hydrogenation processes.

EXAMPLE 2
Preparation of Ethyl (+) (R)-4-chloro-3-hydroxybutyrate 100 g of ethyl 4-chloro-3-oxobutyrate and 64.9 mg of {[Ru (p-cymene) I (+) TMBTP] I}, prepared in example 1, are placed under argon in a 3-liter reactor, in 1000 ml of ethyl alcohol degassed with argon; the mixture is heated at 120° C. under argon and pressurised with hydrogen at 5 bar. After 3 h, the mixture is cooled, concentrated at reduced pressure, and the residue distilled with 5 mm Hg vacuum. 91 g of ethyl (+) (R)-4-chloro-3-hydroxybutyrate are obtained with an e.e. of 97% by gas-chromatography analysis.

EXAMPLE 3

Preparation of L-carnitine 8.4 g (0.05 mol) of ethyl (+) (R)-4-chloro-3-hydroxybutyrate and 23 ml (0.18 mol) of 45% trimethylamine in H$_2$O are placed in a 50 ml-vial. The vial is closed with a rubber plug, sealed with a ring cap and maintained at 80° C. for 24 h. At the end of the reaction the vial is cooled and opened. The aqueous solution is transferred to a flask, 20 ml of methylene chloride are added and the resulting solution is left overnight under stirring. The aqueous phase is then recovered and eluted on a chromatography column containing 200 ml of Amberlite IRA 402 resin activated in the form of HCO$_3$—.

After elution of the first 30 ml, carnitine is eluted. The fractions containing L-carnitine (TLC analysis using CHCl$_3$ 42, isopropyl alcohol 7, methyl alcohol 28, H$_2$O 10.5, AcOH 10.5 as eluent), approximately 100–150 ml, are united and vacuum-concentrated. Isobutyl alcohol is used to form the azeotrope with water and completely eliminate the water.

The hygroscopic solid thus obtained is triturated with acetone and kept overnight under stirring with acetone. Filtration is performed and L-carnitine obtained with a final yield of 70%.

EXAMPLES 4–7

The hydrogenation procedure described in example 2 was repeated, changing the S:C ratios (Table 1), or operating with catalytic amounts of base (Table 2).

The results obtained are as follows:

TABLE 1

Hydrogenation reaction on 10 g catalyst:{[Ru(p-cymene) I (+) TMBTP]I} scale

| Test | T | P | S:C | % conv/t | Conc. | e.e. | yield |
|---|---|---|---|---|---|---|---|
| 4 | 120° C. | 5 bar | 5000:1 | 100%/30 min | 10% | 96% | 97% |
| 5 | 120° C. | 5 bar | 10000:1 | 100%/30 min | 10% | 96% | 98% |

Legends:
S:C: substrate:catalyst molar ratio
% conv/t: percentage substrate reduced/time
conc.: substrate concentration in reaction mixture
e.e.: optical purity of reduced product The results in Table 1 show that, when operating with the catalysts described in the present invention, and under the reaction conditions indicated, it is possible to obtain ethyl 4-chloro-3-hydroxybutyrate in high yields and with high-grade enantiomeric optical purity.

TABLE 2

| | | Hydrogenation reaction on 100 g catalyst:{[Ru(p-cymene) I (+) TMBTP]I} scale | | | | | | |
|---|---|---|---|---|---|---|---|---|
| Test | Base | T | P | S:C | % conv/t | Conc. | e.e. | Yied |
| 6 | No | 120° C. | 5 bar | 10000:1 | 100%/240 min | 10% | 96% | 95% |
| 7 | Yes | 120° C. | 5 bar | 10000:1 | 100%/70 min | 10% | 95% | 92% |

EXAMPLE 8

Preparation of Ethyl (+) (R)-4-chloro-hydroxybutyrate

14 Kg of ethyl 4-chloro-3-oxobutyrate (titre 88%) and 6.2 g of {[Ru (p-cymene) I (+) TMBTP] I}, are placed under argon in a 200-liter reactor, in 143 l of ethyl alcohol. The mixture is heated at 116° C. and pressurized with hydrogen at 5–6 bar. Temperature rises up to 124° C. and the reaction goes to completion within about 1 hour. The mixture is cooled, concentrated at reduced pressure, and the residue, analyzed with gaschromatography, has a 81% titre of ethyl (+) (R)-4-chloro-3-hydroxybutyrate, with an e.e. of 96.7% reaction yield: 94%.

EXAMPLE 9

Preparation of L-carnitine 400 g of crude ethyl (+) (R)-4-chloro-3-hydroxybutyrate, prepared according to Example 8, and 1 l of 45% trimethylamine in $H_2O$ are placed in a 2-liter reactor. The reaction mixture is heated to 80° C. and kept at this temperature for 15 h. After cooling and removing the excess of trimethylamine under nitrogen flow, the aqueous solution is extracted with 1.9 l of methylene chloride and analyzed with HPLC. L-carnitine is obtained with 75% yield.

EXAMPLE 10

Preparation of L-carnitine 110 g of ethyl (+) (R)-4-chloro-3-hydroxybutyrate, prepared according to Example 2, and 280 ml of 45% trimethylamine in $H_2O$ are placed in a 0.6-liter reactor. The reaction mixture is heated to 80° C. and kept at this temperature for 2 h. After cooling and removing the excess of trimethylamine, the aqueous solution is extracted with 0.5 l of methylene chloride and analyzed with HPLC. L-carnitine is obtained with 71% yield.

What is claimed is:

1. A process for the synthesis of L-carnitine comprising the following steps:
   (a) enantioselectively reducing an alkyl 4-chloro-3-oxobutyrate or 4-chloro-3-oxobutyramide according to the following diagram:

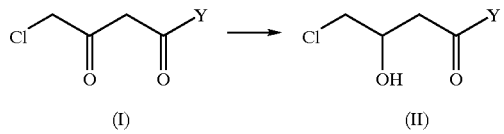

where:
Y is $OR_1$, NH—$R_1$, or N($R_1R_2$) in which $R_1$ and $R_2$, which may be the same or different, are alkyl $C_1$–$C_{10}$ alkylaryl, and where the reduction reaction catalyst consists of a ruthenium complex corresponding to one of the two formulas (III) or (IV)

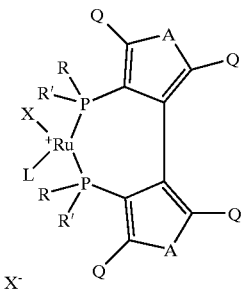

(III)

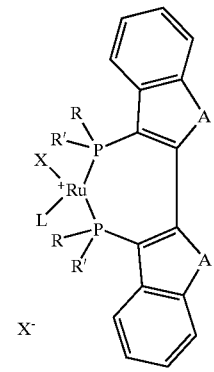

(IV)

where:
A is S in formula (III) and A is $NR_3$ in formula (IV),
$R_3$ is $C_1$–$C_{10}$ alkyl,
Q is $C_1$–$C_4$ alkyl,
R, R', which may be the same or different, are optionally alkyl-substituted phenyl, $C_1$–$C_6$ alkyl, $C_3$–$C_8$ cycloalkyl or R and R' together form a 4–6 atom phosphorocyclic system,
X and L, are the same or different, in which X is halogen, alkylsulphonate, or arylsulphonate, and L is halogen, aryl, π aryl, an olefin system, or carboxylate;
provided at least one of X or L is halogen;
wherein said reduction is performed at a hydrogen pressure ranging from 2 to 7 bar, a temperature ranging from 90 to 150° C. and at a substrate: catalyst molar ratio ranging from 10,000:1 to 30,000:1;
(b) reacting the formula (II) derivative obtained in step (a) with trimethylamine to form L-carnitine.

2. A process according to claim 1, wherein the substrate concentration in the reaction mixture of step (a) ranges from 5 g/100 ml to 15 g/100 ml.

3. A process according to claim 2, where reduction (a) is performed at a hydrogen pressure of 5 bar; at temperature 120° C.; a substrate:catalyst molar ratio of 10,000:1 to 20,000:1; and a substrate concentration in the reaction mixture 10 g/100 ml.

4. A process according to claim 1, where the reaction mixture in step (a) contains catalytic amounts of an organic base.

5. A process according to claim 4, in which the organic base is selected from the group consisting of pyridine, alkylpyridine, dimethylaminopyridine, quinoline, alkyiquinoline, 1,4-diazabicyclol[2,2,2]octane and 1,8-diazabicyclo [5,4,0]undecene.

6. A process according to claim 5, in which the amount of the base used is 0–5% per each mole of alkyl 4-chloro-3-oxobutyrate or 4-chloro-3-oxobutyramide used.

7. A process according to claim 1, where reaction (b) is carried out at a temperature of 65° C. for 60 hours.

8. A process according to claim 1, where reaction (b) is carried out at a temperature of 80° C. for 1–24 hours.

9. A process according to claim 1, where the L-carnitine obtained in (b) is purified.

10. A process according to claim 1, where the catalyst is {[Ru (p-cymene) I (+) TMBTP] I}, represented by the following formula:

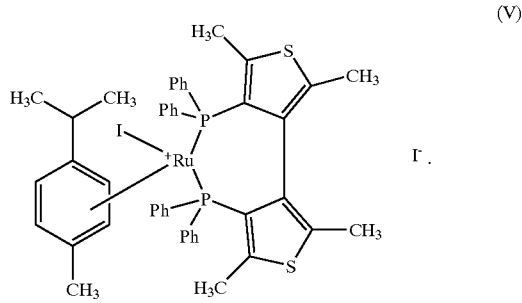

(V)

11. A process according to claim 1, wherein the compound (I) or (II) has a purity of at least 88%.

* * * * *